United States Patent
Soliman et al.

(10) Patent No.: US 9,750,515 B2
(45) Date of Patent: Sep. 5, 2017

(54) AUTOMATICALLY ADJUSTING PATELLA CUTTING GUIDE

(71) Applicant: Howmedica Osteonics Corp., Mahwah, NJ (US)

(72) Inventors: Mohamed Soliman, Englewood, NJ (US); Troy Allen McMillen, Milford, PA (US); Robert J. Leonard, Rockaway, NJ (US)

(73) Assignee: Howmedica Osteonics Corp., Mahwah, NJ (US)

( * ) Notice: Subject to any disclaimer, the term of this patent is extended or adjusted under 35 U.S.C. 154(b) by 764 days.

(21) Appl. No.: 14/172,262

(22) Filed: Feb. 4, 2014

(65) Prior Publication Data

US 2014/0155903 A1    Jun. 5, 2014

Related U.S. Application Data

(62) Division of application No. 12/903,470, filed on Oct. 13, 2010, now Pat. No. 8,728,087.

(51) Int. Cl.
*A61B 17/15*    (2006.01)
*A61B 17/17*    (2006.01)

(52) U.S. Cl.
CPC ........ *A61B 17/1767* (2013.01); *A61B 17/158* (2013.01); *Y10T 29/539* (2015.01)

(58) Field of Classification Search
CPC . A61B 17/154; A61B 17/158; A61B 17/1677; A61B 17/1764; A61B 17/1767; A61F 2/461; A61F 2/3877; A61F 2002/4622; A61F 2002/4628; B25B 5/04; B25B 5/064; B25B 5/163; B25B 1/2426; B25B 1/2431; B25B 1/2447; B25B 1/2478; B25B 7/04; B25B 13/28; B25B 13/30; B25B 13/32; B25B 13/505
See application file for complete search history.

(56) References Cited

U.S. PATENT DOCUMENTS

| | | |
|---|---|---|
| 838,514 A | 12/1906 | Baker |
| 2,528,814 A | 11/1950 | Boyer |
| 4,633,862 A | 1/1987 | Petersen |
| 4,673,862 A | 6/1987 | Wahlstrom |
| 5,147,365 A | 9/1992 | Whitlock et al. |
| 5,222,955 A | 6/1993 | Mikhail |
| 5,284,482 A | 2/1994 | Mikhail |
| 5,486,177 A | 1/1996 | Mumme et al. |

(Continued)

*Primary Examiner* — Kevin T Truong
*Assistant Examiner* — Tracy Kamikawa
(74) *Attorney, Agent, or Firm* — Lerner, David, Littenberg, Krumholz & Mentlik, LLP

(57) ABSTRACT

A patella clamping device has a handle having a first arm and a second arm, the arms each having a first gripping end and a second clamping end. The clamping ends are movable towards the opposite arm by action on the gripping end of each arm. The clamping ends of the first and second arms comprise opposed clamping surfaces. The clamping end of each arm has a body portion having spaced first and second surface defining the opposed surface of each arm. A plurality of pins extend from the first to the second surface. A rotatable toothed jaw member is pivotally mounted on each of the pins. The jaw member has at least one tooth extending outwardly of the opposed surface of each arm for engaging the patella. Each body has a third surface spaced from the second surface to create a slot for receiving a saw blade.

8 Claims, 8 Drawing Sheets

(56) References Cited

U.S. PATENT DOCUMENTS

| | | |
|---|---|---|
| 5,542,947 A | 8/1996 | Treacy |
| 5,716,362 A | 2/1998 | Treacy |
| 6,010,509 A | 1/2000 | Delgado et al. |
| 6,159,217 A | 12/2000 | Robie et al. |
| 7,566,335 B1 | 7/2009 | Scott et al. |
| 7,632,279 B2 | 12/2009 | Bastian |
| 2006/0142777 A1 | 6/2006 | Bastian |
| 2007/0162031 A1 | 7/2007 | Hogg et al. |
| 2007/0188141 A1 | 8/2007 | Hamaguchi et al. |
| 2007/0233142 A1 | 10/2007 | Oliver |
| 2008/0114366 A1 | 5/2008 | Smucker et al. |

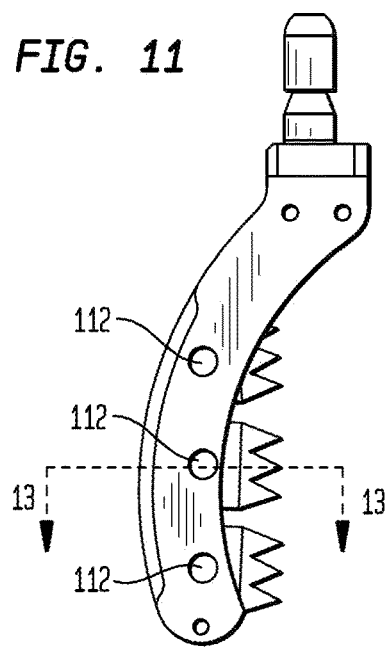
FIG. 11
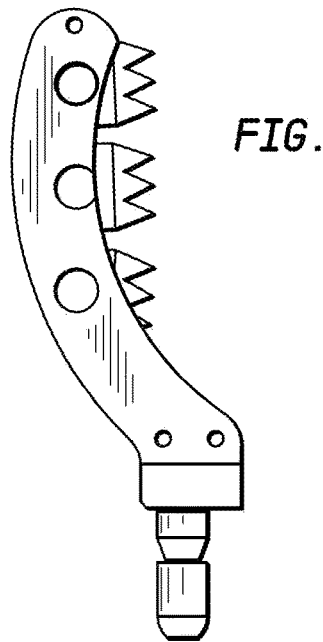
FIG. 12
FIG. 13
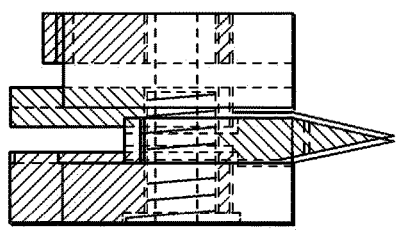

AUTOMATICALLY ADJUSTING PATELLA CUTTING GUIDE

CROSS-REFERENCE TO RELATED APPLICATIONS

This application is a divisional of U.S. application Ser. No. 12/903,470 filed Oct. 13, 2010, the disclosures of which are incorporated herein by reference.

BACKGROUND OF THE INVENTION

The invention relates to a patellar saw guide which has a plurality of rotatable teeth adapted to engage an edge of a patella prior to its preparation for receiving a prosthetic implant.

A patellar clamp and saw guide are used during a total knee arthroplasty procedure to prepare the posterior surface of a patellar bone to accept a prosthetic implant.

Typically, a surgeon will select a patellar prosthesis for implantation either by utilizing a resurfacing technique wherein the prosthetic patella will be resected and resurfaced and/or by an insetting procedure where the prosthetic patella is inserted into the prepared surface of the patella.

The patella is a sesamoid or lens shaped bone which slides in a groove between the condyles of the femur. Its function is to increase the efficiency of the quadriceps muscle by shifting the line of action of the muscle's pull forward. As the knee articulates, the muscles and tendons force the patella toward the condyles of the femur. Consequently, there is considerable relative motion between the patella and the other bones comprising the knee joint.

Because of aging or disease, the articulating surfaces of the knee may degrade. To treat certain pathologies, it has become common to surgically remove the condyles and replace these structures with prosthetic implants. By the same processes, the articulating surfaces of the patella may also degrade. In connection with the implantation of a prosthetic knee, therefore, the articulating surface of the patella may also be replaced. Because of the tendons connected to the patella, it is generally advisable to replace only the articulating surfaces. An ultra high molecular weight polyethylene articulating surface, with or without a metal baseplate or metal backing, will be implanted on the posterior side of the patella, adjacent the femoral condyles.

In either a total resurfacing procedure or a patella insetting procedure, it is important that a sufficient amount of bone stock remain after resection to accept the typical fixation pegs of the patellar prosthesis and maintain the integrity of the remaining patellar bone. Therefore, proper location of the saw blade is important.

As used herein, when referring to bones or other parts of the body, the term "proximal" means closer to the heart and the term "distal" means more distant from the heart. The term "inferior" means toward the feet and the term "superior" means towards the head. The term "anterior" means towards the front part of the body or the face and the term "posterior" means towards the back of the body. The term "medial" means toward the midline of the body and the term "lateral" means away from the midline of the body.

Prior art devices for aiding the surgeon in performing patella resections are well known to those skilled in the art. For example, Peterson, in U.S. Pat. No. 4,673,862, teaches a method and instruments for the installation of a patella button prosthesis which involves performing a patella resection.

In particular, Peterson relates to a saw guide which comprises a pliers-like instrument having a pair of mutually pivotable jaw members. The jaw members are designed so as to enable them to surround part of the outer periphery of the patella with each jaw member having a respective handle, integrally formed therewith, which handles may be pivoted so as to pivot the jaw members to and from engagement with part of the patella periphery. The Peterson device requires that a flat saw blade be guided over the face of the jaw members after the patella has been set to the correct depth between the members.

U.S. Pat. No. 5,147,365 relates to a patella osteotomy guide in which the jaw members include a slot for guiding the flat saw blade and an arm for setting the saw blade depth in the patella.

U.S. Pat. No. 5,486,177 relates to a patella milling instrument having a clamp which contacts the underside of the patella. A similar clamping tool is shown in U.S. Pat. No. 5,284,482.

U.S. Pat. No. 5,222,955 relates to a reaming system designed to cut a conical bore in a patella surface while the patella is being held in a patella clamp similar to that disclosed in U.S. Pat. No. 5,284,482. U.S. Pat. No. 5,941,884 relates to a patella clamp which includes indicia of both the amount of bone resected and the amount of bone remaining.

BRIEF SUMMARY OF THE INVENTION

It is one aspect of the invention to provide an improved apparatus and method for facilitating the preparation of the natural patella to receive a patellar prosthesis.

It is an additional aspect of the invention to provide a clamping system which can hold the patella in position during resection by actuating a pliers like grip.

The cutting guide of the present invention has the ability to clamp variously shaped patellae by automatically adjusting the direction of the clamping teeth to the anatomy of the patella. The intention of this design is to automatically adjust to the edge surface of variously shaped patellae to provide a more secure hold.

The invention works by clamping the patella jaws over the patella bone with multiple teeth embedded in the patella. The patella jaws secure the patella sufficiently to allow a surgeon to use an oscillating surgical saw to resect the patella bone in a well known manner.

The clamping tooth or teeth are located on a plurality of rotatable elements that rotate about a pin such that the teeth will align with the patella edge surface resulting in more holding teeth penetrating the patella bone. The clamp may also have a slot to guide an oscillating surgical saw to cut the clamped patella.

The rotation of the toothed rotatable element is limited by stops placed in a top and/or bottom portion forming the automatically adjusting patella cutting guide. These stops in combination with the stop features cut into each toothed rotatable element limit the amount of rotation of each toothed rotatable element. This limit prevents the 360° rotation of the toothed element about the pin which would allow the teeth to rotate out of contact with the patella bone.

The patella clamping device of the invention has a handle portion having a first arm and a second arm which arms may be coupled by a pivot pin or a linkage system which preferably moves the arms in parallel. The first and second arms each have a first gripping end and a second clamping end. The clamping end of each arm is movable, such as by the pivoting or linkage action, towards the opposite arm by movement of the gripping end of each arm towards one another. The clamping end of the first arm has a clamping surface opposed to a clamping surface on the clamping end of the second arm. The clamping end of each arm includes a body portion having spaced first and second surfaces and a plurality of pins extending from the first surface to the second surface on each arm clamping end. One toothed rotatable jaw member is pivotally mounted on each of the plurality of pins. The rotatable jaw members each have at least one tooth extending outwardly of the opposed surface of each arm towards the opposite arm clamping surface. The opposed clamping surface on the clamping arm defined by the body portion may be arcuate with a concave surface facing towards the patella gripping area. Each body portion preferably has three pins and toothed rotatable jaw members. Each jaw preferably has three teeth but fewer or more teeth can be used. To improve gripping at least two teeth on each jaw may have a different size or shape. Each body portion may include a stop element adjacent each toothed jaw member to limit the rotation of each toothed rotatable jaw member around the pin. The stop member may be a raised portion on at least one of the first and second surfaces adjacent a recessed side surface of the toothed jaw member. The first and second clamping arm bodies have a surface for guiding a saw blade.

BRIEF DESCRIPTION OF THE DRAWINGS

FIG. 11 is a top view of an assembly of the clamping arm bottom portions, top portion and toothed element of FIGS. 4, 7 and 9 respectively;

FIG. 12 is a bottom view of the assembly FIG. 11;

FIG. 13 is a cross-sectional view of the clamping arm member shown in FIG. 11.

DETAILED DESCRIPTION

Figure 1:
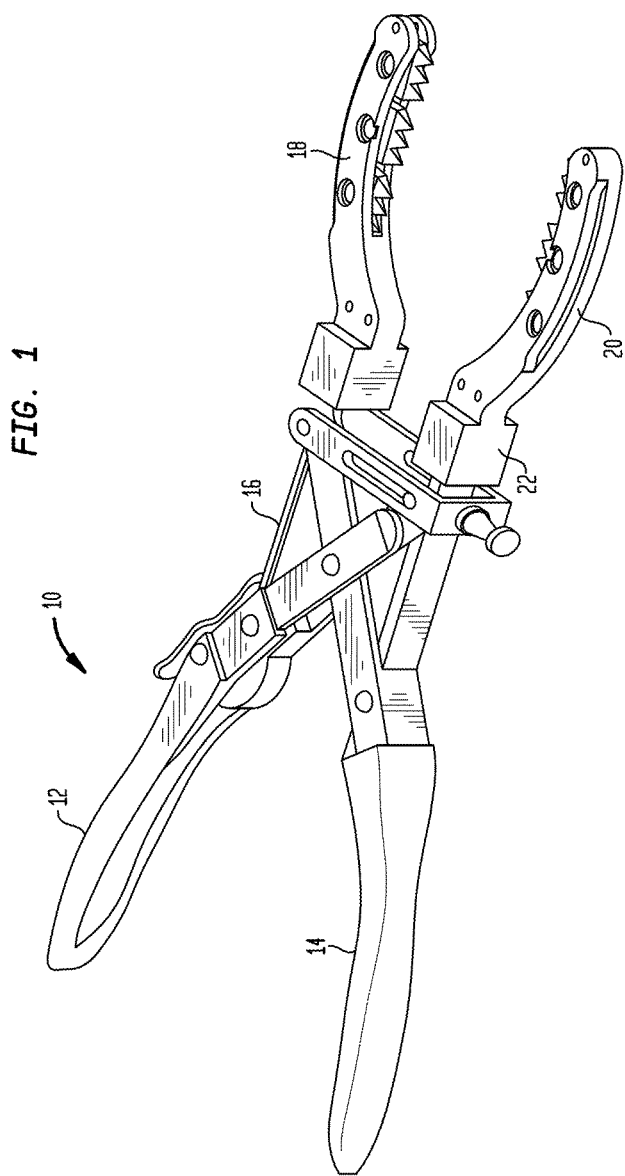
FIG. 1 is an isometric view of a patella clamp including the automatically adjusting clamps of the present invention.

Referring to FIG. 1, there is shown a patella clamping device generally denoted as 10 which includes a handle portion including two gripping members 12 and 14. Gripping members 12 and 14 engage a pivot section 16 which is capable of moving a first jaw arm 18 towards a second jaw arm 20. Pivot section 16 may include one or more pivot pins and/or a linkage system for transferring the action or gripping member 12, 14 to jaw arms 18, 20. The linkage system may move jaw arms 18, 20 in parallel. The jaw arms 18 and 20 may be removably coupled to clamping section 16. The handle portion and pivot section of the patella clamping device 10 are known in the prior art and are shown, for example, in U.S. Patent Application Publication No. 2007/0118141, the disclosure of which is incorporated herein by reference.

Figure 2:
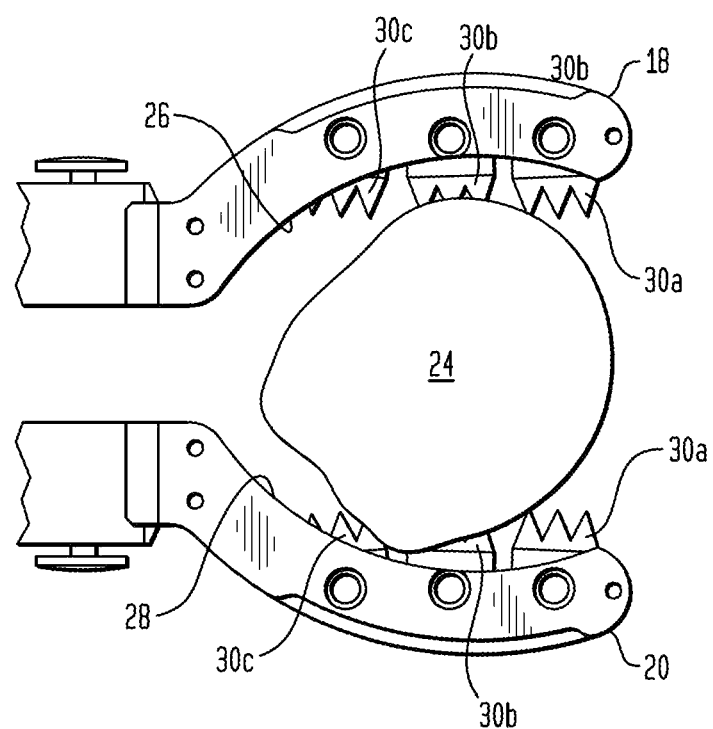
FIG. 2 is a plan view of the clamping end of the clamping device of FIG. 1 gripping the peripheral edge surfaces of a patella.
Figure 3:
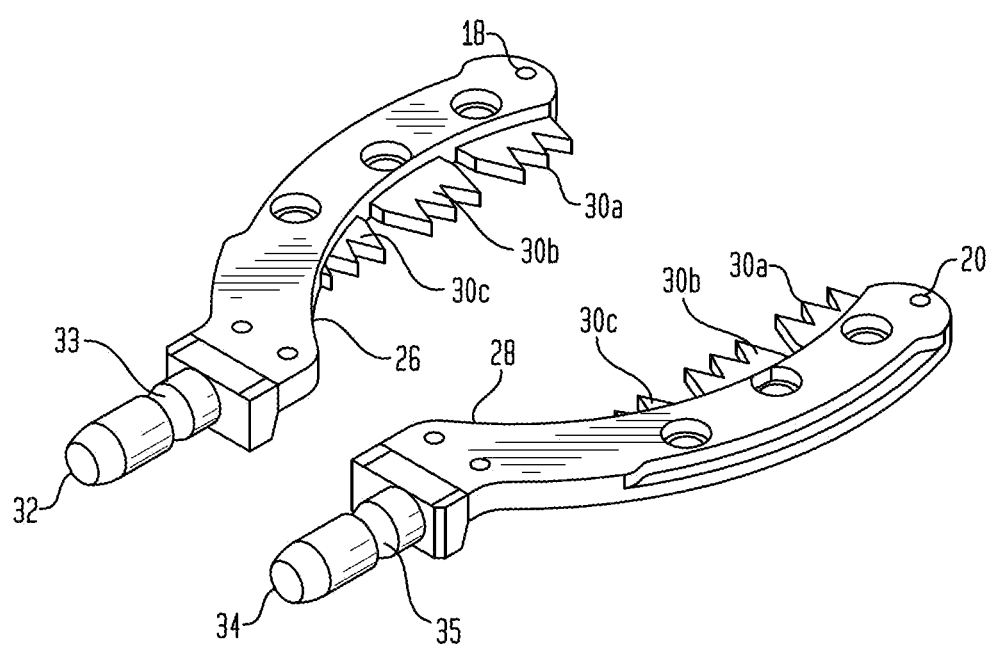
FIG. 3 is an enlarged view of the two patella clamps shown in FIG. 2 detached from the clamping device of FIG. 1.

Referring to FIG. 2, there is shown a top view of the two clamping jaw arms 18 and 20 surrounded and clamping a patella 24. Arms 18 and 20 are arcuate and have concave surfaces 26 and 28 respectively facing inwardly towards patella 24 which arms include rotatable toothed jaw elements 30a, 30b and 30c which will be discussed in more detail below. Arms 18 and 20 may be separate elements which can be selectively coupled or detached from pivot section 16. Referring to FIG. 3, there is shown the clamping jaw arms 18 and 20 detached from the handle portion of clamping device 10. At the end mounted on the handle 10 there are coupling elements 32 and 34 designed to couple the clamping jaw arms to the handle 10 in a selectively releasable manner. Preferably two spring loaded detent mechanisms (not shown) which respectively engage recessed portions 33 and 35 of elements 32 and 34 are mounted in ends 17 and 19 of pivot section 16. Obviously the jaws could be fixedly attached to the handle 10. However, providing a releasable coupling mechanism allows for different size clamping jaws to be used depending on the size of a patella. Preferably each clamping arm 18, 20 includes a series of three pivotable tooth elements 30a, 30b and 30c each having, in a preferred embodiment, three teeth.

Figure 4:
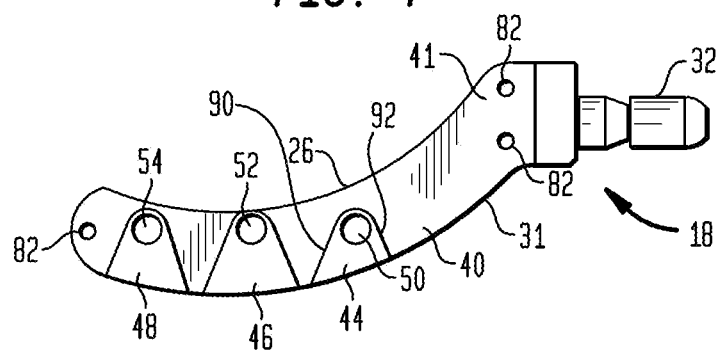
FIG. 4 is a plan view of a bottom portion of each clamp arm of FIG. 3.
Figure 5:
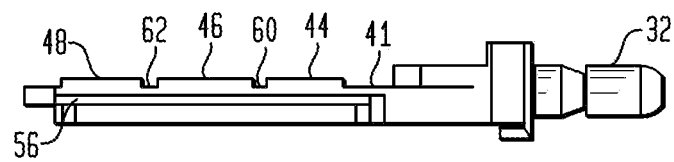
FIG. 5 is an elevation view of the clamping arm bottom portion shown in FIG. 4.

Referring to FIGS. 4-8, there is shown bottom portion 40 (FIGS. 4-7) and top portion 42 (FIGS. 7 and 8) respectively which, when assembled, form clamping jaw arms 18 and 20. Only one claiming jaw 18 is described. Clamping jaw is identical in design but concave in the opposite direction. Thus clamping jaw arms 18 and 20 are mirror images. Referring to FIG. 4, there is shown a top view of bottom portion 40 of clamping jaw arms 18 and 20 including coupling element 32. Bottom portion 40 includes three raised areas or bosses 44, 46 and 48 which have a generally triangular shape with the apex directed towards the concave surface 26 of the arm 18. Each boss 44, 46 and 48 has a bore 50, 52 and 54 respectively which may be located on a centerline of the raised areas adjacent the apex which bores are adjacent concave surface 26. The bosses 44, 46 and 48 can be seen in FIG. 5 which is an elevation view of jaw arm 18 of FIG. 4. Also visible in FIG. 5 is a cutting blade slot 56 below an upwardly facing surface 41 of bottom portion 40. Slot 56 may receive an oscillating saw blade (not shown) adapted to resect the patella in a well known manner.

Figure 6:
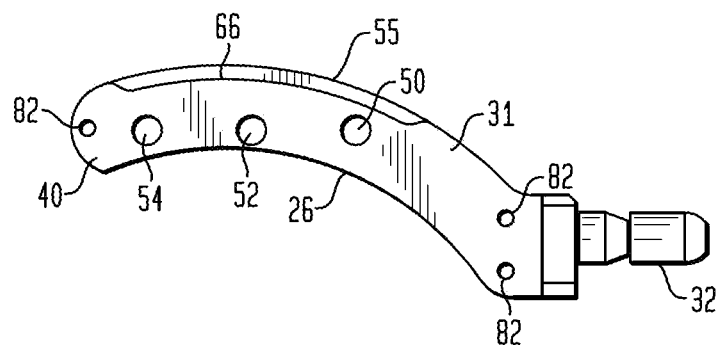
FIG. 6 is a bottom view of the clamping arm bottom portion of FIG. 4.

As best seen in FIG. 5 bosses 44, 46 and 48 are separated by gaps 60 and 62 which gaps widen on moving from the outer surface 31 of jaw arm 18 to the inwardly facing surface 26 of bottom portion 40 of arm 18. Referring to FIG. 6 there is a bottom view of jaw arm 18 bottom portion 40 showing bores 50, 52 and 54 as well as a recessed edge 66 which defines an upper surface 55 of slot 56.

Figure 7:
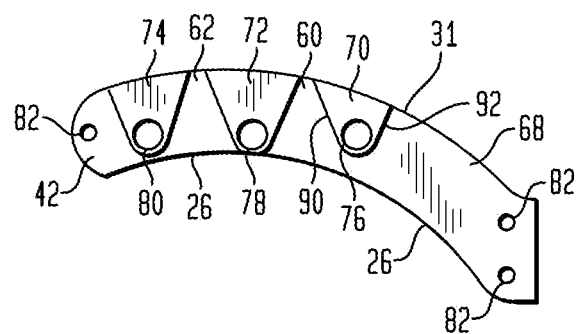
FIG. 7 is a top view of a clamping arm top portion as shown in FIG. 3.
Figure 8:
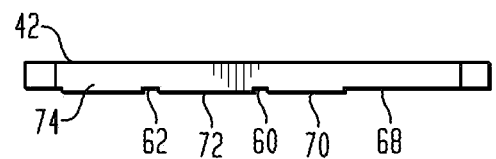
FIG. 8 is an elevation view of the clamping arm top portion shown in FIG. 7.

Referring to FIGS. 7 and 8 there is shown top portion 42 of clamping jaw arm 18. Top portion 42 includes a downwardly facing surface 68 which includes three bosses 70, 72 and 74 which again are generally triangular in shape and match the shape of bosses 44, 46 and 58. The apexes of bosses 70, 72 and 74 are adjacent concave surface 26 and wider portions adjacent outer surface 31. Three pin holes 76, 78 and 80 are located adjacent the apex on each boss. Top portion 42 includes three small holes 82 designed to receive holding pins which connect the bottom and top portions (40, 42) of arms 18 and 20 such as by spot welding or deformation. Top portion 42 does not include a coupling element 32 and generally acts to mount and capture rotatable toothed jaw elements 30a, 30b and 30c.

Each of the generally triangular shaped bosses 44, and 48 and 70, 72 and 74 can be aligned prior to the assembly of the top and bottom portions to form clamping jaw arm 18. Thus, each aligned pair of bosses have identical angled sides 90 and 92 so that upon assembly a smooth side surface of the aligned bosses result. When bosses 44, 46 and 48 are aligned respectively with bosses 70, 72 and 74 holes 50, 52 and 54 are also aligned with holes 76, 78 and 80 so that they may receive a pivot pin 112. Side surfaces 90 and 92 of each of the six bosses are angled at between 40 and 45 degrees and spaced to form gap 60 and 62. These angles can change based on teeth size and boss size. For example, a larger boss would create a smaller angle. In a preferred embodiment, the alignable bosses 44 and 70 as well as alignable bosses 46 and 72 have sides 90 and 92 angled at 45 degrees while alignable bosses 48 and 74 having an angle of sides 90 and 92 of 40 degrees. In addition, the lengths of sides 90 and 92 of the bosses may vary depending on the location of alignable holes 50, 52, 54 and 76, 78 and 80 which holes, when the top and bottom portions 40 and 42 are assembled, align to receive a pivot pin as will be discussed below.

FIG. 8 is an elevation view of top portion 42 of FIG. 7 showing bosses 70, 72 and 74 spaced by gaps 60 and 62.

Figure 9:
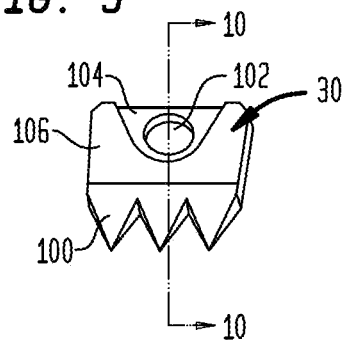
FIG. 9 is an isometric view of a rotatable toothed element for mounting between the bottom clamping arm portion of FIG. 4 and the top clamping arm portion of FIG. 7.
Figure 10:
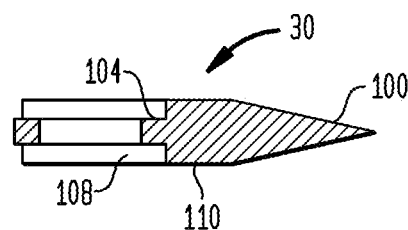
FIG. 10 is a cross-sectional view through lines X-X of FIG. 9.
Figure 10A:
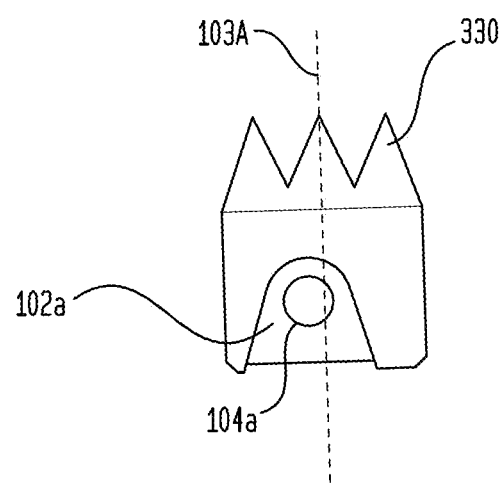
FIG. 10a is an alternate embodiment of the rotatable toothed element wherein the hole is moved outward of the center line of the element to allow more rotation of the teeth inwardly.

Referring to FIGS. 9 and 10, there is shown one of the rotatable toothed elements 30a, 30b and 30c each including three teeth 100. While three teeth 100 are shown, any number of teeth can be utilized. FIG. 9 shows one of the toothed element 30a, 30b and 30c which may be identical and is designated as 30 including a bore 102 for receiving a pivot pin and a recessed generally triangular area 104 facing an upper surface 106 and, as seen in FIG. 10, a bottom recessed generally triangular area 108 facing a bottom surface 110. Bore 102 may be located on a centerline of a toothed element 30a, 30b and 30c. However, as shown in FIG. 10a, an alternate toothed element 130 may have a bore 102a offset from a centerline 103a so that greater inward rotation of teeth 100a is permitted. This result can also be accomplished by leaving bore 102a in the center but offsetting the pivot pin holes 76, 78 and 80 in the bosses.

Toothed elements 30a, 30b, 30c and 130 are adapted to be mounted between the top and bottom members 40, 42 of clamping jaw arms 18, 20. The top and bottom recessed areas 104 and 108 are shaped to receive bosses 44, 46, 48 and 70, 72 and 74 when the top and bottom jaw arm portions 40, 42 are assembled. However, the generally triangularly shaped recessed areas 104, 104a and 108 of toothed elements 30a, 30b, 30c and 130 are at a wider angle than the 40 to 45 degree included angle of sides 90 and 92 of each boss 44, 46, 48, 70, and 74 thus allowing limited rotation of the toothed elements about pivot pin 112 mounted through holes 50, 52, 54 and 76, 78, 80 respectively and bore 102. The sides of the bosses act as stop surfaces so that toothed elements 30a, 30b, 30c and 130 cannot rotate out of engagement with the patella.

Referring to FIGS. 11-13, there is shown the assembled clamping jaw arms 18 or 20 whereby bottom portion and top portions 40, 42 are assembled capturing toothed elements 30a, 30b and 30c therebetween. Holding pins (not shown) extending through holes 82 may be spot welded to each top and bottom portion 40, 42 to capture toothed element 30 therebetween. Three pivot pins 112 are inserted through holes or bores 76, 78 and 80 of top portion 42, through bore 102 of each toothed element 30a, 30b, 30c and into bores 50, 52 and 54 of bottom portion 40. Pins 112 may be spot welded to top member 42. Pins 112 extend partially into bottom member 40 stopping prior to slot 56 thus leaving the slot 56 open to receive an oscillating saw blade (not shown).

In use, clamping jaw arms 18 and 20 are mounted on portion 16 of clamping device 10 and handles 12 and 14 are actuated to clamp the clamping jaw arms 18, 20 around a patella. Upon contacting an edge surface of the patella, at least one of the three toothed jaw elements on each clamping arm 18 and 20 will pivot automatically into a position engaging the periphery of patella 24. Thus, a plurality of teeth 100 from one or more of the tooth elements will contact each side of the periphery of the patella.

The teeth 100 of toothed elements 30a, 30b, 30c or 130 may be made either identically or may vary in size either on each toothed element 30a, 30b and 30b or from one toothed element to another. Again this enhances the ability to have multiple teeth 100 contacting the edge of patella 24. Once the patella 24 is gripped, a resection may be performed with an oscillating saw in a standard manner.

Figure 14:
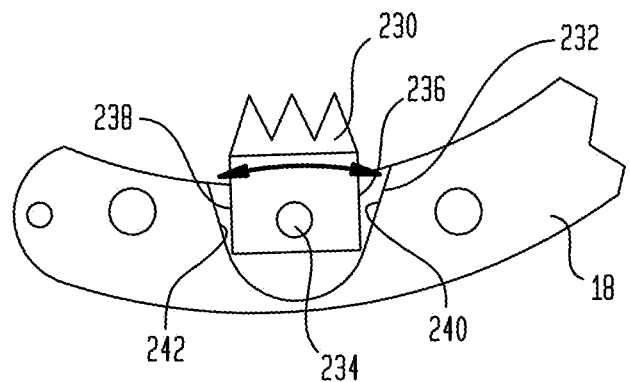
FIGS. 14 and 15 show alternate embodiments of jaw rotation stop elements.

Referring to FIG. 14, there is shown a jaw member 230 similar to jaw members 30a, 30b and 30c mounted on an arm 18, 20 in a recess 232 formed thereon. The recess 232 is similar in shape to the bosses described above. Jaw 230 is again rotatable on a pivot pin 234 with contact between sides 236 and 238 of jaw member 230 and sides 240 and 242 of recess 232 acting as a stop system for the rotation of jaw 230 about pivot pin 234.

Figure 15:
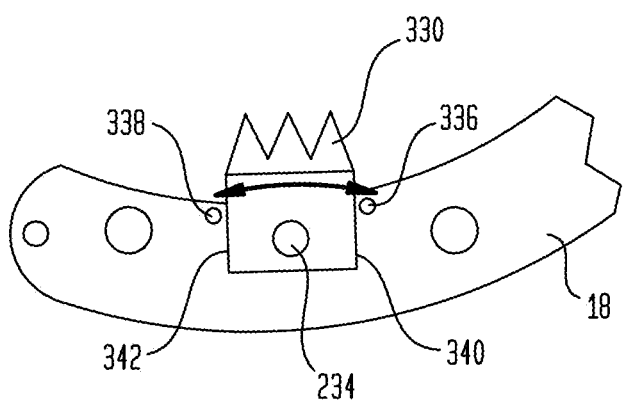

Referring to FIG. 15, there is shown a jaw member 330 mount on an arm 18, 20 rotatable about a pivot pin 334. In this embodiment there are no bosses or recesses but only two pins 336 and 338 for contact side surfaces 340 and 342 of jaw 330 to act as stop elements. Pins 336 and 338 would be fixed to members 40 and 42 and extend between surfaces 41 and 68 thereof.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A patella clamping device comprising:
first and second opposed arcuate patella clamping arms each having a free end, a concave surface facing the opposed clamping arm, and first and second spaced surfaces;
a plurality of toothed jaw members for engaging the patella on each of the first and second arcuate patella clamping arms, each of the plurality of jaw members pivotally mounted on one of a plurality of pivot pins extending between the first and second spaced surfaces of a respective one of the first and second clamping arms, the teeth on each of the plurality of jaw members extending inwardly towards the concave surface of the opposed clamping arm, each of the plurality of jaw members having an upper surface and a lower surface and first and second side surfaces connecting the upper and lower surfaces, the first and second spaced surfaces on each of the first and second clamping arms having a plurality of stop pins extending therebetween, each stop pin having a first end and a second end mounted on a respective one of the first and second spaced surfaces of the respective clamping arm, each stop pin spaced from the respective one of the plurality of pivot pins, wherein the first and second side surfaces of each jaw member each interact with a respective one of the plurality of stop pins to act to limit the pivoting of each jaw member; and a means for moving clamping ends of the opposed first and second clamping arms toward one another, the plurality of jaw members located intermediate the free end of the respective clamping arm and the means for moving the clamping ends of the opposed first and second clamping arms toward one another, and wherein each of the first and second clamping arms includes spaced parallel third and fourth surfaces defining a slot for guiding a saw blade, the slot located between both the first and second spaced surfaces and an outer surface of each respective clamping arm.

2. The patella clamping device as set forth in claim 1 wherein the plurality of pivot pins on each clamping arm includes three pivot pins spaced between the respective clamping arm free end and the means for moving.

3. The patella clamping device as set forth in claim 1 wherein each jaw member has three teeth.

4. A patella clamping device comprising:

first and second opposed arcuate patella clamping arms pivotally connected to one another, each of the first and second clamping arms having a free end, a concave surface facing the opposed clamping arm, and first and second spaced surfaces;

a plurality of toothed jaw members for engaging the patella on each of the first and second arcuate patella clamping arms, each of the plurality of jaw members pivotally mounted on a pivot pin extending between the first and second spaced surfaces of a respective one of the first and second clamping arms, the teeth on each of the plurality of jaw members extending inwardly towards the concave surface of the opposed clamping arm, each of the plurality of jaw members having an upper surface and a lower surface and first and second side surfaces connecting the upper and lower surfaces; and a means for moving the opposed first and second clamping arms toward one another, the plurality of jaw members located intermediate the free end of the respective clamping arm and the means for moving the opposed first and second clamping arms toward one another, and wherein each of the first and second clamping arms includes spaced parallel third and fourth surfaces defining a slot for guiding a saw blade, the slot located between both the first and second spaced surfaces and an outer surface of the respective clamping arm, wherein the first and second spaced surfaces on each of the first and second opposed clamping arms include a plurality of stop pins extending therebetween, each stop pin having a first end and a second end mounted on a respective one of the first and second spaced surfaces of the respective clamping arm, each of the plurality of stop pins having a surface engaging a respective one of the first and second side surfaces of a respective one of the plurality of toothed jaw members to limit the pivotal movement of the respective one of the plurality of toothed jaw members, wherein each of the plurality of stop pins is spaced from the pivot pin on which the respective one of the plurality of toothed jaw members is mounted and limits the pivotal movement of the respective one of the plurality of toothed jaw members.

5. A patella clamping device comprising:

a handle having a first arm and a second arm pivotally connected to one another for pivoting about a pivot axis, the first and second arms each having a first gripping end and a second clamping end, the clamping end of each of the first and second arms movable towards the clamping end of the other of the first and second arms, by action on the gripping end of each arm, the clamping end of the first arm having a clamping surface opposed to a clamping surface on the clamping end of the second arm, the clamping end of each of the first and second arms comprising a curved body portion having a first end closer to the first gripping end of the respective first or second arm, a free end, spaced first and second surfaces extending in a direction perpendicular to the pivot axis, and at least two pivot pins extending from the first surface to the second surface on the respective curved body portion of each of the first and second arms; and a jaw member pivotally mounted on each of the at least two pivot pins intermediate the first end and the free end of the curved body portion of each of the first and second arms, each jaw member having at least one tooth for engaging the patella extending outwardly of the clamping surface of each of the first and second arms towards the curved body portion of the other of the first and second arms, each jaw member having spaced upper and lower surfaces and first and second side surfaces extending between the upper and lower surfaces, the spaced first and second surfaces on each of the curved body portions having at least four stop pins extending therebetween, wherein the first and second side surfaces of each jaw member interface with a respective two of the at least four stop pins to limit rotation of the jaw member about the respective pivot pin, each stop pin having a first end and a second end mounted on a respective one of the spaced first and second surfaces of the respective curved body portion and spaced from the respective pivot pin, and wherein each curved body portion includes spaced parallel third and fourth surfaces defining a slot for guiding a saw blade, the slot located between both the first and second surfaces and an outer surface of the respective curved body portion.

6. The patella clamping device as set forth in claim 5 wherein the at least two pivot pins on each curved body portion includes three pivot pins spaced between the respective curved body portion free end and the respective gripping end.

7. The patella clamping device as set forth in claim 6 wherein each jaw member has three teeth.

8. The patella clamping device as set forth in claim 7 wherein at least two teeth on each jaw member have a different size.

* * * * *